(12) United States Patent
Means

(10) Patent No.: US 6,436,656 B1
(45) Date of Patent: Aug. 20, 2002

(54) METHOD FOR SCREENING A TEST COMPOUND FOR POTENTIAL AS AN IMMUNOSUPPRESSIVE DRUG CANDIDATE

(75) Inventor: Anthony R. Means, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/033,715

(22) Filed: Mar. 3, 1998

Related U.S. Application Data

(60) Provisional application No. 60/038,558, filed on Mar. 3, 1997.

(51) Int. Cl.[7] .............................. C12Q 1/48; C12Q 1/00
(52) U.S. Cl. ............................................. 435/15; 435/4
(58) Field of Search ....................... 435/15, 4

(56) References Cited

PUBLICATIONS

Kitani et al., "Inactivation of Ca2+/Calmodulin–dependent protein kinase IV by Ca2+/Calmodulin and restoration of the activity by Mg2+/EGTA", J. Biochem., 117(5):1070–1075, May 1995.*

Park et al., "Activation of Ca2+/Calmodulin–dependent protein kinase (CaM–kinase) IV by CaM–kinase kinase in Jurkat T lymphocytes", J. Biol. Chem., 270(51):30464–30469, Dec. 1995.*

Chatila et al., "A unique phosporylation–dependent mechanism for the activation of Ca2+/Calmodulin–dependent protein type IV/GR", J. Biol. Chem., 271(35):21542–21548, Aug. 1996.*

Chatila et al, "A Unique Phosphorylation–dependent Mechanism for the Activation of $Ca^{2+}$/Calmodulin–dependent Protein Kinase Type IV/GR", The Journal of Biological Chemistry 271(35):21542–21548 (1996).

Tokumitsu et al, "Activation Mechanisms for $Ca^{2+}$/Calmodulin–dependent Protein Kinase IV", The Journal of Biological Chemistry 269(46):28640–28647 (1994).

Sikela et al, "Chromosal Localization of the Human Gene for Brain $Ca^{2+}$Calmodulin–Dependent Proten Kinase Type IV", Genomics 4:21–27 (1989).

Sun et al, "Organzation and Analysis of the Complete Rat Calmodulin–dependent Protein Kinase IV Gene", The Journal of Biological Chemistry 270(49):29507–29514 (1995).

Sikela et al, "Genetic Mappying of the Gene for $Ca^{2+}$/Calmodulin–Dependent Protein Kinase IV (Camk–4) to Mouse Chromosome 18", Genomics 8–579–582 (1990).

Jones et al, "cDNA sequence and differential expression of the mouse $Ca^{2+}$/calmodulin–dependent protein kinase IV gene", FEBS Letters 289(1):105–109 (1991).

Okuno et al, "Evidence for the Existence of $Ca^{2+}$/Calmodulin–Dependent Protein Kinase IV Kinase Isoforms in Rat Brain", J. Biochem. 119–1176–1181 (1996).

Tokumitsu et al, "Characterization of a $Ca^{2+}$/Calmodulin–dependent Protein Kinase Cascade", The Journal of Biological Chemistry 270(33):19320–19324 (1995).

Enslen et al, "Characterization of $Ca^{2+}$/Calmodulin–dependent Protein Kinase IV", The Journal of Biological Chemistry 269(22):15520–15527 (1994).

Sakagami and Kondo, "Cloning and sequencing of a gene encoding the β polypeptide of $Ca^{2+}$/calmodulin–dependent protein kinase IV and its expression confined to the mature cerebellar granule cells", Molecular Brain Research 19:215–218 (1993).

Kitani et al, "Inactivation of $Ca^{2+}$/Calmodulin–Dependent Protein Kinase IV by $Ca^{2+}$/Calmodulin and Restoration of the Activity by Mg2+/EGTA", J. Biochem. 117:1070–1075 (1995).

Butler et al, "Limbic epilepsy in transgenic mice carrying a $Ca^{2+}$/calmodulin–dependent kinase II α–subunit mutation", Proc. Natl. Acad. Sci. USA 92:6852–6855 (1995).

* cited by examiner

Primary Examiner—Deborah Crouch
Assistant Examiner—Joseph T. Woitach
(74) Attorney, Agent, or Firm—Nixon & Vanderhye P.C.

(57) ABSTRACT

The present invention relates, in general, to immunosuppression and, in particular, to a method of inducing an immunosuppressive effect. The invention further relates to a method of screening compounds for immunosuppressive activity.

7 Claims, 11 Drawing Sheets

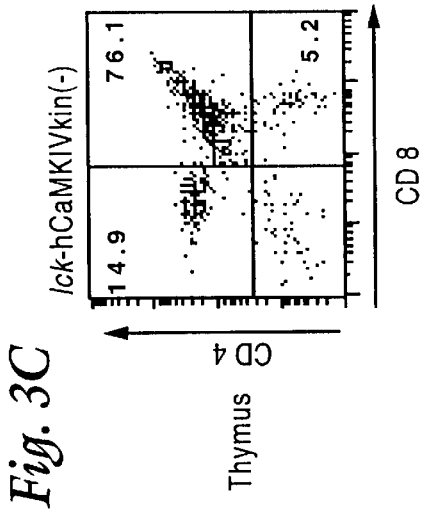
*Fig. 3A* *Fig. 3B* *Fig. 3C*
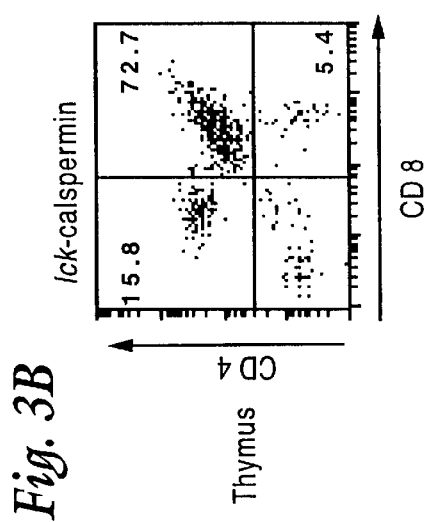
*Fig. 3D* *Fig. 3E* *Fig. 3F*
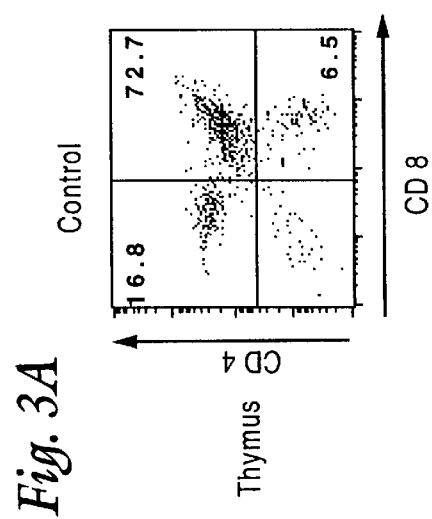

control thymocytes

*lck*-CaMKIVkin(−) thymocytes

Utilizing an EcoRI site 3' of the CaM kinase IV wild type locus ATG start site, digestion with EcoRI and SacI yields a fragment of 1.9 kb. Homologous recombination of the neo cassette removes the EcoRI site and the next unique site is an upstream SacI, thereby resulting in a 5.1 kb SacI fragment when using the probe shown.

METHOD FOR SCREENING A TEST COMPOUND FOR POTENTIAL AS AN IMMUNOSUPPRESSIVE DRUG CANDIDATE

This application claims priority from Prov. Appln. No. 60/038,558, filed Mar. 3, 1997, which is incorporated in its entirety by reference.

This invention was made with Government support under Grant No. HD-07503 awarded by the National Institutes of Health and Grant No. 5F32AIC9258-02 awarded by Public Health Service. The Government has certain rights in the invention.

TECHNICAL FIELD

The present invention relates, in general, to immunosuppression and, in particular, to a method of inducing an immunosuppressive effect. The invention further relates to a method of screening compounds for immunosuppressive activity.

BACKGROUND $Ca^{2+}$/calmodulin-dependent protein kinase IV (CaMKIV) is a monomeric multifunctional enzyme that is expressed only in subanatomical portions of the brain, T lymphocytes and postmeiotic male germ cells. It is present in the nucleus of cells in which it is expressed (Jensen et al, Proc. Natl. Acad. Sci. USA 88:2850 (1991)). CaMKIV phosphorylates and activates the cyclic AMP response element binding proteins CREB and CREMτ in a manner analogous to protein kinase A (Matthews et al, Mol. Cell. Biol. 14:6107 (1994); Sun et al, Genes Dev. 8:2527 (1994); Enslen et al, J. Biol. Chem. 269:15320 (1994)).

In the absence of $Ca^{2+}$/calmodulin, CaMKIV is inactive. Activation requires three events: i) binding of $Ca^{2+}$/calmodulin; ii) phosphorylation of a single threonine residue present in the activation loop by a separate protein kinase that is also $Ca^{2+}$/calmodulin-dependent; and iii) autophosphorylation of serine residues present in the extreme N-terminus that is required to relieve a novel form of autoinhibition.

The gene for rat CaMKIV has been cloned and found to span 42 kb of DNA. The gene encodes 3 proteins namely, the α and β forms of CaMKIV that differ only in that the β form contains a 28 amino acid N-terminal extension as well as calspermin (Sun et al, J. Biol. Chem. 270:29507 (1995)). Calspermin is the C-terminal 169 amino acids of CaMKIV that binds $Ca^{2+}$/calmodulin and is expressed only in posmeiotic male germ cells. The promoter for calspermin resides in the penultimate intron of the CaMKIV gene and is regulated by two CREs. Available data suggest that rearrangement of chromatin during meiosis together with the expression of CREMτ at high levels are sufficient to control expression of the calspermin promoter during spermatogenesis. On the other hand, the developmental expression of CaMKIV in cells of the brain and T cells appears to be controlled by thyroid hormone mediated via the thyroid hormone receptor α.

Prior to the present invention, the specific role of CaMKIV in T cell activation had not been defined and the potential importance of CaMKIV as a target for immunosuppressive agents had not been suggested. Indeed, currently available immunosuppressive drugs, as well as new generation drugs presently under development, target calcineurin. Since calcineurin is present in all cells, not just T cells, these drugs are associated with a plethora of side effects. The present invention provides a method of identifying immunosuppressive agents that target CaMKIV and that are T cell specific and thus substantially free of adverse side effects.

OBJECTS AND SUMMARY OF THE INVENTION

It is one object of the invention to provide a method of inducing an immunosuppressive effect, while avoiding undesirable side effects.

It is another object of the invention to provide a method of screening compounds for immunosuppressive activity.

It is a further object of the invention to provide a method of inhibiting CREB phosphorylation specifically in T cells.

The foregoing objects are met by the present invention which results, at least in part, from the recognition that inhibition of CaMKIV prevents phosphorylation of CREB and thereby activation of T cells.

Further objects and advantages of the present invention will be clear from the description that follows.

BRIEF DESCRIPTION OF THE DRAWINGS

FIGS. 1A and 1B. Diagramatic representation of the two transgenes used to generate transgenic mice. FIG. 1A depicts the hCaMKIV construct and the amino acid substitution used to generate the kinase inactive form. FIG. 1B shows the calspermin construct. FIGS. 1C and 1D. Southern blot analysis of transgenic mice. FIG. 1C depicts two founding lines of hCaMKIVkin(−) mice while FIG. D shows one of three founding lines of the calspermin overexpressing mice. FIGS. 1E–1G. Expression of endogenous CaMKIV, hCaMKIVkin(−), and calspermin. FIG. 1E shows the expression of CaMKIV in a control mouse(center lane) and from the two different founding lines (left lane is line K; right lane is line I). FIG. 1E shows the expression of calspermin in one of the founding lines of mice [note that the calspermin antibody also recognizes CaMKIV]. FIG. 1G shows expression of the hCaMKIVkin(−) in thymic T cells from line I transgenic mice utilizing an antibody that only recognizes the human form of CaMKIV. Expression of the hCaMKIV is absent in transgenic splenocytes as well as in control thymic and splenic cells.

FIGS. 2A and 2B. Cellularity of thymi and survival of thymic T cells from transgenic mice. Cells were harvested, counted and plated for survival assays. FIG. 2A depicts the cellularity of the thymus from both transgenic lines and a control line of mice (n=14; P<0.01). FIG. 2B shows the rate of survival in culture of these same cells (n=34; P<0.01). FIGS. 2C and 2D. Cellularity and survival of splenocytes that were isolated and treated identically as were the thymic T cells.

FIGS. 3A–3F. Distribution of CD4 and CD8 T cells. Cells were isolated from thymi and spleens of transgenic and control mice and stained for flow cytometry using PE conjugated anti-CD4 and FITC conjugated anti-CD8 antibodies. FIGS. 3A–3C show the distribution of cells from the thymus while FIGS. 3D–3F show the distribution of cells from the spleen. This Figure is representative of the results obtained from 6 independent experiments.

FIGS. 4A–4D. Thymocytes and splenocytes from control and lck-CaMKIVkin (−) transgenic mice were either unstimulated (uns) or stimulated with PMA+ionomycin or with a-CD3 for 1, 5, and 30 min. Cell lysates were then subjected to western blot analysis using antibody specific for CREB phosphorylated on Ser-133 (a-pCREB) or antibody recognizing both phosphorylated and unphosphorylated CREB (a-CREB). The arrow indicates the position of CREB. The faster migrating inducible band is tentatively identified as ATF-1. Shown is one representative experiment. (n=9). FIGS. 4E and 4F. Thymocytes and splenocytes from lck-calspermin transgenic mice were either unstimulated or stimulated with PMA+ionomycin for 5 and 30 min. Levels of phosphorylated CREB were then determined as described in FIGS. 4A–4D. Shown is one representative experiment. (n=2).

FIG. 6A. IL-2 induction. IL-2 secretion from control and lck-CaMKIVkin(−) and lck-calspermin transgenic thymocytes was quantified after stimulation for 48 h with PMA+ionomycin. Values represent the average ±SD of one representative experiment performed in triplicate (n=5). FIGS. 6B–6D. IL-2Ra (CD25) induction. Thymocytes from control and lck-CaMKIVkin(−) and lckcalspermin transgenic mice were stained for CD25, and analyzed by FACS on a flow cytometer before (unshaded curve) and after stimulation for 30 h with PMA+ionomycin (shaded curve). Shown is one representative experiment. (n=4).

DETAILED DESCRIPTION OF THE INVENTION

Figure 1B:
FIGS. 1A–1G.

CaMKIV is expressed exclusively in subanatomical portions of the brain (particularly enriched in mature granule cells), meiotic (but not mitotic) male germ cells and lymphocytes of thymic origin (ie T cells). A primary target for CaMKIV in mature T cells is the transcription factor CREB. Phosphorylation of CREB by CaMKIV (at Ser-133) results in transcriptional activation of the intermediate early genes (members of the fos and jun families) which are responsible for activation of genes encoding cytokines, such as interleukin 2 (IL-2). The production of IL-2 is required for activation of T cells by serving as a requisite mitogen. The present invention is based on the realization that inhibition of CaMKIV-dependent phosphorylation of CREB in T cells results in immunosuppression. This realization and the fact that the only cells other than T cells that express CaMKIV are protected by a blood brain barrier (ie testis and brain), make possible the identification of T-cell-specific immunosuppressants.

The present invention relates to a method of screening compounds for immunosuppressive activity. In one embodiment, the method comprises:
i) contacting CaMKIV and a substrate therefor, in the presence and absence of a test compound, under conditions such that CaMKIV-dependent phosphorylation of the substrate can be effected, and
ii) determining, directly or indirectly, the level of phosphorylation of the substrate,
wherein a reduction in phosphorylation of the substrate in the presence of the test compound is indicative of an immunosuppressive agent.

The method of the invention can be carried out in a cell free system or using cells in culture.

Advantageously, a test compound is screened for immunosuppressive activity first in a cell free system and subsequently in an intact cell system. Cell free systems can include, in addition to CaMKIV and substrate, CaMKIV kinase, calmodulin and calcium, as well as a phosphate donor. The concentrations of the various system components can vary, however, one skilled in the art can readily optimize reaction conditions based on the guidance provided in the Examples that follow. The reaction can be carried out in a standard kinase buffer, such as those described in the Examples that follow and in the citations incorporated herein by reference.

The substrate used in the cell free system is advantageously a peptide substrate. While CREB can be used, alternative substrates, such as syntide-2 from Bachem, can also be employed. Phosphate donors suitable for use in the present invention include ATP, a radiolabeled form, such as [$\gamma$-$^{32}$P]ATP, being preferred.

The effect of the test compound on the CaMKIV-dependent phosphorylation can be determined using a variety of approaches well known in the art. When $^{32}$P-ATP is used as the phosphate donor, the extent of phosphorylation of the substrate can be determined by monitoring the amount of $^{32}$P associated with the substrate.

In a specific embodiment of the above-described method, a test compound is tested for its ability to competitively inhibit CaMKIV phosphorylation of a peptide substrate (e.g., GS10); standard protein kinase assays can be used (see generally Selbert et al, J. Biol. Chem. 270:17616 (1995)). For example, a reaction mixture comprising the test compound, the peptide substrate, CaMKIV, calcium, calmodulin, CaMKIV kinase and phosphate donor (e.g., bearing a detectable label, such as a radioactive label) is prepared and incubated under conditions such that the kinases present in the mixture can effect phosphorylation of their respective substrates (a constitutively activated form of CaMKIV can be used in the reaction mixture in lieu of CaMKIV, in which case the CaMKIV-activating components (e.g., CaMKIV kinase) need not be present). The reaction mixture is then processed so as to eliminate labeled phosphate not associated with substrate (i.e., non-incorporated labeled phosphate). For example, the reaction mixture can be applied to an ion exchanger, for example, an ion exchange filter (e.g., a P81 filter). The ion exchanger (e.g., filter) is then washed and the amount of detectable label associated therewith determined and compared with the amount of detectable label associated with a control ion exchanger (i.e., an ion exchanger to which a reaction mixture as described above but minus test compound, is applied). A reduction in the amount of detectable label associated with the ion exchanger (and thus with substrate) in the presence of the test compound (relative to the control) is indicative of an immunosuppressive agent.

CaMKIV must bind Ca$^{2+}$/calmodulin to be active. Further, CaMKIV must be phosphorylated on Thr-200 (in the human form of the enzyme) by CaMKIV kinase. This phosphorylation can be readily detected, for example, by separating the components of the reaction mixture (as described above), for example, on a polyacrylamide gel, and quantifying the amount of detectable label incorporated into CaMKIV, for example, by phosphoimaging. Since phosphorylation of CaMKIV is required for CaMKIV activation, a test compound that inhibits CaMKIV kinase can also be expected to be an effective immunosuppressive agent. The effect of a test compound on the phosphorylation events (e.g., phosphorylation of CaMKIV by CaMKIV kinase or phosphorylation of CaMKIV substrate by CaMKIV) can be measured in a single reaction. To effect this simultaneous screen, $Ca^{2+}$/calmodulin, CaMKIV kinase, CamKIV, substrate for CaMKIV and labeled phosphate donor (e.g., $^{32}P$ ATP) can be combined with a standard protein kinase assay reaction mixture. After incubation, an aliquot of the resulting reaction mixture is applied, for example, to a P81 filter and processed as described above for determination of CaMKIV substrate phosphorylation. This provides an assessment of CaMKIV activity. A further aliquot is, for example, run on a polyacrylamide gel and the amount of labeled phosphate incorporated into the CaMKIV quantified, for example, by phosphoimaging. This provides an assessment of CaMKIV kinase activity. CaMKIV is the only known substrate of the CaMKIV kinase, except for CaMKI. At present, CaMKI does not have a known physiological function. (See generally assay details provided in Selbert et al, J. Biol. Chem. 270:17616 (1995)).

As indicated above, test compounds screened in the cell free system can also be screened using a system based on cells in culture. Cells that contain CREB and CaMKIV naturally (eg T cells) can be used in such screens, as can cells resulting from engineering. Mammalian as well as non-mammalian engineered cells can be used, lymphocytes or fibroblasts transfected with a CaMKIV encoding sequence being examples, as are yeast cells transfected with sequences encoding the required proteins. (See Sun et al, Genes & Develop. 8:2527 (1994).) Cells can be stimulated using a variety of approaches, including use of a calcium ionophore or occupancy of the T cell receptor. As in the case of the cell free system, the immunosuppressive activity of a test compound can be determined by assessing the extent to which the substrate (e.g., CREB) is phosphorylated. While a variety of techniques can be used (including quantitating the transfer of $^{32}P$ from a radiolabeled phosphate donor to the substrate), the use of antibodies specific for the phosphorylated form of the substrate (e.g., antibodies specific for the phosphorylated form of CREB) is preferred (see 33).

Compounds demonstrated to have immunosuppressive activity based on one or more of the above-described screens can be modified as appropriate to minimize toxic effects and the like. Since T cell specificity is desired, immunosuppressive compounds can also be derivatized, if necessary, to ensure that they do not cross the blood brain/testis barrier.

Screening procedures such as those described above are useful for identifying agents for their potential use in pharmacological intervention strategies including those in which FK506 and cyclosporin A are typically employed. Examples of areas in which such agents will find applicability include treatment of autoimmune diseases, including multiple sclerosis, rheumatoid arthritis, and systemic lupus erythematosis, and treatment of patients undergoing organ and tissue (including bone marrow) transplantation.

The present invention also relates to pharmaceutical compositions comprising, as active agent, compounds selected using one or more of the above-described screening protocols. Such compositions include the active agent(s) in combination with a pharmaceutically acceptable carrier. The amount of active agent in the composition can vary with the agent, the patient and the effect sought. Likewise, the dosing regimen, including mode of administration, will vary depending on the composition and the disease/disorder to be treated.

Certain aspects of the present invention are described in greater detail in the non-limiting Examples that follow. One skilled in the art will appreciate from a reading of the foregoing and the Examples that the transgenic animals described herein can be used to screen compounds for immunostimulatory potential.

EXAMPLES

The following experimental details relate to specific Examples that follow (numbers in parentheses refer to References below).

Materials

Phorbol-12 myristate-13 acetate (PMA) and ionomycin were obtained from Calbiochem (La Jolla, Calif.). [125I] protein-A, [a-32P]deoxy-CTP and ECL chemiluminescent reagents were purchased from Amersham (Arlington Heights, Ill.). Phycoerythrocin and FITC conjugated antibodies for the murine CD4, CD8, and CD25 complexes as well as all tissue culture reagents came from Gibco (Grand Isle, N.Y.). Anti-calspermin antibodies were produced in rabbits housed on site at the Duke University vivarium and had characteristics similar to the antibodies described by Ono et al. (29). A bacterially expressed form of the rat calspermin protein was utilized as the antigen. Two independently derived anti-CaMKIV polyclonal antibodies were also obtained. One was a gift from Talal Chatila (17) the other generated commercially by Immuno-Dynamics Incorporated (La Jolla, Calif.). Both antibodies were produced in rabbits against identical synthetic peptides that consisted of the C-terminal 17 amino acids of the human form of CaMKIV. Anti-CREB and anti-phosphoCREB antibodies were obtained from Upstate Biotechnology Incorporated (Lake Placid, N.Y.). ELISA reagents for the measurement of murine interleukin-2 (IL-2) production as well as the anti-aCD3 monoclonal antibody (145.2C11) were provided by Pharmingen (San Diego, Calif.). All other reagents were of molecular biology grade unless otherwise specified Transgene Construction and Generation of Mice Targeted expression of the transgenes to murine thymocytes was accomplished by utilizing the shuttle vector p1017 [a gift from R. Perlmutter, University of Washington, Seattle] (25). This vector contains the sequence for the mouse proximal lck promoter plus additional sequence derived from the human growth hormone gene (hGH) and has been shown to initiate high level expression of cDNAs specifically in thymic T cells of transgenic mice (27). A 1.5 Kb cDNA for the human form of Ca2+/calmodulin dependent protein kinase type IV (hCaMKIV) that had been mutated to result in a catalytically inactive protein (23) and a 0.5 Kb cDNA for the rat form of calspermin (29) were isolated from plasmids by the appropriate restriction digests and subcloned separately into a BamHI site between the lck promoter and the hGH sequences of the p1017 vector as represented diagramatically in FIG. 1A. After confirming that the cDNAs were in the correct orientation by DNA sequencing, the transgenes were linearized and isolated by restriction digestion with NotI (Boehringer Mannheim, Indiana, Ind.) followed by electrophoresis in a 1% agarose gel (FMC Corp., Rockland, Md.). Both transgenes were purified from the agarose using Prep-a-Gene (Bio-Rad, Richmond, Calif.), aliquoted in 10 mM Tris and 0.1 mM EDTA buffer and stored at −20 C. for subsequent microinjection.

B6SLF1/J mice (Jackson Laboratories, Bar Harbor, Me.) were used to generate the transgenic mice, because they produce excellent yields of viable eggs for microinjection [Cheryl Bock, Director of the Duke Transgenic Core Facility, personal communication]. Ovulation of female mice, male stud service, collection of eggs, microinjection of DNA and reimplantation of fertilized eggs was done following standard methods previously described (50) and was performed by the Duke Comprehensive Cancer Center Transgenic Core Facility. Mice that expressed the correct DNA fragment as determined by Southern blot analysis were then bred to nontransgenic B6SLF1/J mice in order to establish viable lines for analysis. All mice were housed at the Duke Cancer Center Isolation Facility under a 12 hour light-dark cycle. Food and water were provided ad libidum and all care given to the mice was in compliance with the NIH guidelines for the care and use of laboratory animals.

DNA and RNA Analysis

Genotyping of founder mice and subsequent generations of mice was done as previously described by Southern blot analysis (51). In this procedure, 10 ug of genomic DNA was digested with SpeI (Boehringer Mannheim) for 12 h at 37 C. electrophoresed through a 1% agarose gel and blotted onto Zeta-Probe membranes (Bio-Rad, Richmond, Calif.). 32P randomly labeled probes were used to confirm the presence of the transgene and to ascertain copy number. For the lck-hCaMKIVkin(−) mice a 500 bp BamHI-BglII fragment derived from the hCaMKIV cDNA 3+ end was utilized as the probe. In the case of the lck-calspermin transgene we utilized the entire 522 bp cDNA encoding rat calspermin. It should be noted that the SpeI restriction site used for Southern analysis was engineered into the p1017 plasmid at both the extreme 5+ and 3+ ends (25, 27) and does not exist in the wild type locus for either CaMKIV or calspermin. Hence, while the cDNA probes also hybridized to the wild type locus only a single band was detected in Southern blots because the wild type band was substantially larger than the transgene. Total RNA was isolated from tissue after extraction with Utraspectm total RNA isolation reagent (Biotex Laboratories, Houston, Tex.). RNA was subjected to electrophoresis through 1.5% agarose-formaldehyde gels (5 µg/lane) and blotted onto Zeta-Probe membranes (Bio-Rad, Richmond, Calif.). RNA blots were then hybridized to a 32P randomly labeled cDNA fragment corresponding to the appropriate mRNA. The Fos B probe was made from a 1.6 kb Hind3 fragment of murine Fos B. The GAPDH probe was from a 780 bp Pst1/Xba1 fragment of human GAPDH. Hybridization was carried out in 500 mM sodium phosphate (pH 7.2), 7% sodium dodecyl sulfate (SDS), and 1 mM EDTA at 65 C. for 18 h. Washes were done at 65 C. in 40 mM sodium phosphate and 1% SDS until background level radioactivity was undetectable. Visualization of blots was accomplished by exposure of the blot to Kodak XAR film (Rochester, N.Y.) at −70 C. for up to 24 h.

Primary Cell Culture

Primary cultures of thymic or splenic T cells were established from mice between the ages of 21 and 30 days of age for all experiments. Mice were killed by cervical dislocation and the thymus or the spleen was harvested. Cells were teased from the organs by placing the organs between two pieces of 40xx nytex nylon mesh (Tetko, Kansas City, Mo.) submerged in RPMI-1640 (Gibco, Grand Island, N.Y.) supplemented with 10% fetal bovine serum (FBS), 0.5% penicillin, 0.5% streptomycin, 1×nonessential amino acids and 0.001M 2-mercaptoethanol at 4 C. and gently pushing down on top of the mesh to rupture the organs. The cells were collected from the supernatant fluid and the remaining tissue was removed and discarded. This procedure resulted in a T-cell purity of >95% from the thymus as assessed by flow cytometry. Splenic T cells were not fractionated on columns but were differentiated from B cells based upon the size differential when counting by trypan blue exclusion. This method yielded consistent results and flow cytometry was employed to confirm the presence of large numbers of T cells. After two successive washes in RPMI-1640 media the cells were counted on a hemocytometer by trypan blue exclusion to determine both the number of cells as well as the fraction representing live cells before aliquoting them for experiments.

Survival assays were carried out on aliquots of cells from spleen or thymus. Cells were collected by centrifugation at 1000 rpm for 5 min at 4 C., and resuspended in Dullbeco's modified Eagle's medium (GIBCO, Grand Island, N.Y.) supplemented with 10% FBS and 0.5% penicillin, 0.5% streptomycin. Cells were then recounted on a hemocytometer by trypan blue exclusion, and 4×106 live cells were plated in pentuplicate in 24 well Falcon brand plates (Becton Dickenson, San Jose, Calif.) containing 2 ml of DMEM. The cells were then incubated at 37 C. in 95% 02/5% CO2. After 30 h the cells were harvested and counted on a hemocytometer by trypan blue exclusion to determine the rate of survival.

FACS Analysis

All FACS analyses were carried out at the Duke Comprehensive Cancer Center Flow Cytometry Core Facility. Experiments were analyzed within 24 h after completion using a Becton-Dickinson Model FACScan with data analysis done using the Cell Quest program (Becton-Dickinson, San Jose, Calif.).

CD4/CD8 determinations for thymic and splenic T cells were carried out as previously described (52). Briefly, 1×106 T cells were placed into 10×75 mm tubes (Becton Dickinson, San Jose, Calif.) on ice. The cells were washed 2 times with phosphate buffered saline containing 5% FBS (FACS buffer). The supernatant fluid was aspirated and 100 µl of FACS buffer was added containing either PE conjugated anti-CD4 (diluted 1:50) or FITC conjugated anti-CD8 (diluted 1:50) or both PE-CD4 and FITC-CD8. The reaction was allowed to proceed 20 min at 4 C. before the reaction was terminated by the addition of fresh FACS buffer. Cells were then briefly washed with fresh FACS buffer and pelleted at 1000 rpm 2 times. The cells were then fixed with PBS containing 1% formaldehyde.

Quantification of the murine interleukin-2 (IL-2) receptor on T cells was accomplished by taking an aliquot of 4×106 live cells, dividing them in half, and plating the paired samples containing 2×106 live cells each into 24 well Falcon Brand plates (Becton-Dickinson) containing fully supplemented RPMI-1640. The final volume of each well was then adjusted to 2 ml. One half of each paired cell sample was left unstimulated while the other half was stimulated with PMA (10 ng/ml) and ionomycin (0.5 ug/ml). After 30 h the cells were harvested, washed in FACS buffer as described above, and immunostained for FACS analysis using FITC conjugated anti-CD25 antibody (Gibco, Grand Island, N.Y.) which recognizes the IL-2 receptor α-chain Protein and Cytokine Analysis Detection of proteins on western blot was accomplished by either standard radioactivity methods or by chemiluminescence. Expression of protein from the transgene was examined by first extracting protein from 5×106 T cells isolated from the thymus or spleen in Lammeli buffer (53). These protein samples were then heated to 95 C., loaded onto a 10% polyacrylamide SDS-containing gel and run at 100 v for 2 h or until the dye front reached the bottom. The protein was transferred electrophoretically to Immobilon Membranes (Millipore, Bedford, Mass.). Membranes were blocked for 1 h at room temperature using tris buffered saline (TBS) with 5% dried milk and 0.01% tween 20. Application of the primary antibody for either hCaMKIV or calspermin was then carried out for 2 h at room temperature in TBS followed by 6 washes in TBS containing 0.01% tween 20 (TBSt) lasting 10 min each. 1×106 cpm/ml of [125I] protein-A was then applied for 1 h in TBS containing 5% dried milk and 0.01% tween 20 followed by 6 washes in TBSt for 10 min each. Blots were exposed on Kodak XAR film overnight for visualization. CREB and phosphoCREB detection was accomplished by stimulating 5×106 cells with PMA (10 ng/ml) and ionomycin (0.5 ug/ml) or anti-a-CD3 monoclonal antibody (16 ug/ml) that had been immobilized to 24 well tissue culture plates at 37 C. in 95% $O_2$/5% $CO_2$. At various time points T cells were harvested and lysed in Lammeli buffer as described previously. Proteins were then fractionated by SDS-PAGE on a 10% gel and subjected to western blotting as described above using commercial antibodies from Upstate Biotechnology Incorporated (Lake Placid, N.Y.). ECL chemiluminescent detection (Amersham, Arlington Heights, Ill.) was substituted for [125I] protein-A following the established manufacturers protocols. Blots were quantified by scanning denisomitry on a 445 SI phosphorimager equipped with a personal densitomiter SI (Molecular Dynamics, Sunnyvale, Calif.). Digital analysis of the scans was completed using the program Image Quant v1.1 (Molecular Dynamics, Sunnyvale, Calif.).

To measure production of IL-2, 2×105 T cells were placed into a flat bottom 96 well plate (Corning-Costar,Cambridge, Mass.) containing the RPMI-1640 media previously described. Well volumes were then adjusted to 250 ul and the cells were stimulated at 37 C. in a humidified chamber with PMA (10 ng/ml) and ionomycin (0.5 $\mu$g/ml) or 16 $\mu$g/ml of the anti-α-CD3 monoclonal antibody that had been immobilized onto the plate. After 48 h the media was removed for analysis. ELISA measurements were done following the standard protocol distributed with the ELISA components (Pharmingen, San Diego, Calif.) for measurement of IL-2. Plates were then quantified on a Multiskan MS 96 well plate reader (Lab Systems, Needham Heights, Mass.)

Statistical Analysis

Initial statistics were performed by a two-way analysis of variance utilizing a 95% confidence level. Post-Hoc analysis was completed using either the Student-Newman-Keuls test when analyzing data from all three types of mice or a two tailed Students t test for data derived from just two types of mice. All data are presented as the mean ± standard deviation. A level of significance was accepted when $P<0.05$.

Example I

Generation of Transgenic Mice

Figure 1A:
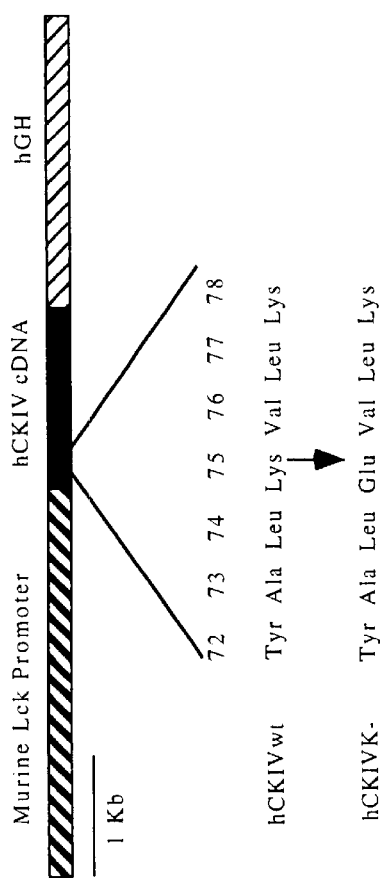

FIG. 1A presents diagrammatic representations of the constructs used to produce transgenic mice. The targeting construct is regulated by the proximal promoter of the murine lck gene and includes sequences of the human growth hormone gene at the 3' end to insure recognition by the splicing machinery. This construct has been shown to direct high level expression of cDNAs cloned between the lck and hGH sequences exclusively in thymic T cells (25, 27). The diagram on the left illustrates the CaMKIV construct. A single mutation was introduced at Lys-75 (Lys to Glu) of the human CaMKIV cDNA that renders the protein catalytically inactive (23, 28). On the right side of FIG. 1A is shown the construct made to produce rat calspermin. Calspermin is a testis specific calmodulin binding protein that is composed of the C-terminal 169 amino acids of CaMKIV (29) and is generated from the CaMKIV gene by utilization of a promoter found in the penultimate intron of the gene (30, 31). Since the kinase inactive CaMKIV retains its high affinity for Ca2+/calmodulin, the calspermin-containing mice were intended to distinguish between any possible dominant/negative effects of the mutant hCaMKIV and effects that might be produced as a consequence of nonspecific Ca2+/calmodulin sequestration. Both CaMKIV and calspermin are localized predominantly in the nucleus.

Genotypic characterization of the transgenic mice is shown by the Southern blots shown in FIG. 1B. The transgenic constructs were generated so that the entire transgene could be removed by digestion with Spe1. This would produce a 6.9 kb fragment from integration of the hCaMKIV transgene and a 5.8 kb fragment from integration of the calspermin transgene. The left panel shows the results of a Southern analysis from DNA extracted from two transgenic and two control mice. It is readily apparent that only the transgenic mice contain a single fragment of the predicted size that hybridizes to the CaMKIV probe. The right panel shows the equivalent experiment carried out on DNA isolated from one transgenic mouse and three control littermates. Again the single predicted fragment is present only in the DNA from the transgenic mouse.

Figure 1C:
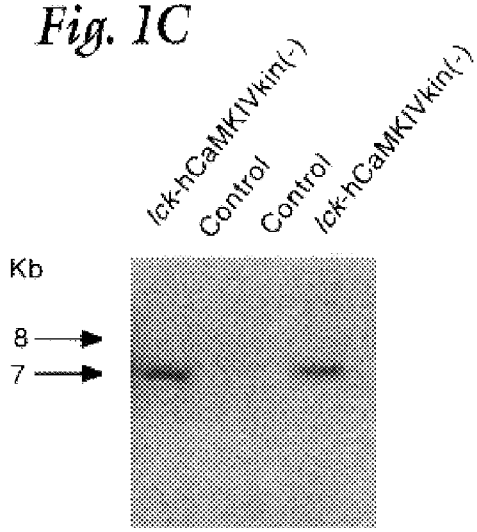
Figure 1D:
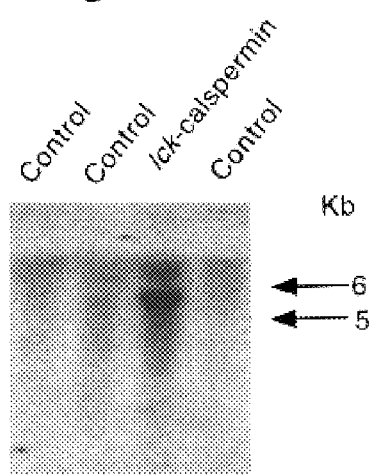
Figure 1E:
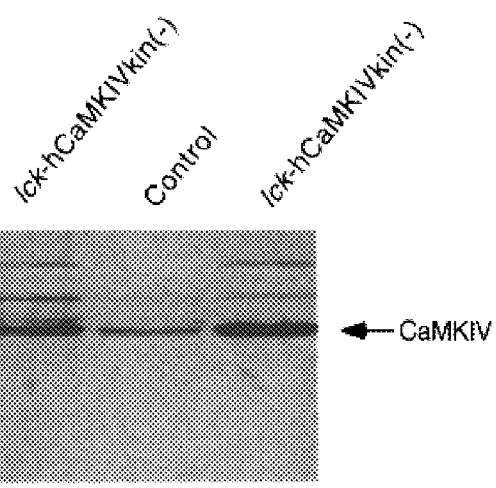
Figure 1F:
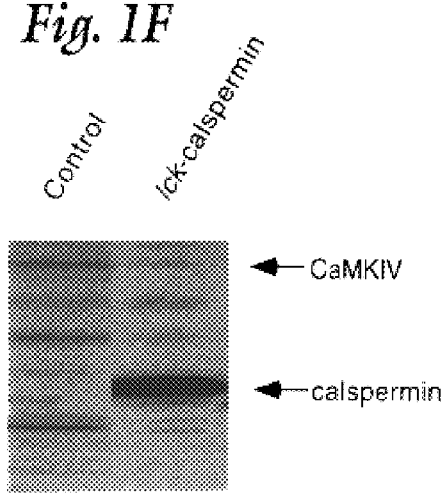
Figure 1G:
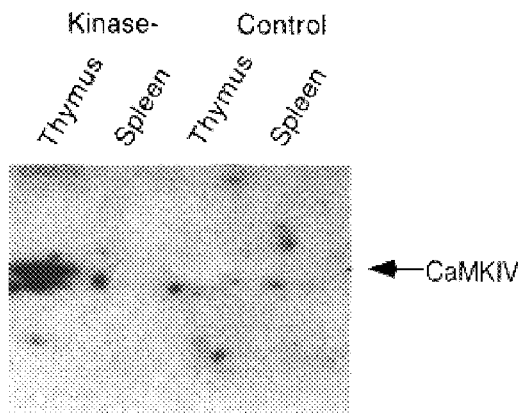

Western blot analysis was used to confirm that the appropriate protein was produced from the respective transgenes. The left panel of FIG. 1C shows the results obtained when an antibody is used that recognizes both the endogenous mouse and transgenically produced human CaMKIV. Thymocyte protein from two transgenic mice flank a similar preparation from a control mouse. It can be seen that the expression level of the transgenic protein is higher in the right lane (Line I) than in the left lane (Line K). Densitometry was used to quantify the difference in protein expression. The amount of immunoreactive CaMKIV in the Line I lane is 4× greater than in the control lane. Thus the thymocytes from Line I produce about a 3× molar excess of the mutant hCaMKIV relative to endogenous levels of the authentic enzyme. Animals from Line I were used in all subsequent experiments. An antibody to a synthetic peptide containing the C-terminal 17 amino acids of hCaMKIV was also prepared that is specific for the human form of the protein. As can be seen in the far left panel of FIG. 1C only T cells resident in the thymus of the transgenic mouse contained the human protein. The fact that no transgenic product is present in thymocytes isolated from the spleen of the identical transgenic mice, is consistent with the fact that the proximal lck promoter is not active once T cells are exported from the thymus (26). Additionally, the absence of the mutant hCaMKIV in splenic T cells implies that this protein must be unstable in these cells.

The center panel of FIG. 1C shows that thymocytes removed from the thymus of one line of transgenic mice produce considerable amounts of calspermin. As there are no amino acids present in calspermin that are not also present in CaMKIV it has not been possible to produce an antibody that recognizes calspermin but not CaMKIV. In addition the isoelectric pH of calspermin is 4.0 and consequently this protein does not transfer quantitatively under the conditions usually employed for Western blots (29). However, examination of the blots suggests that the amount of calspermin present is in considerable excess to the amount of endogenous CaMKIV. Unquestionably the ratio is greater than 3:1. Therefore, these cells can be used to control for any nonspecific effects due to the presence of the mutant hCaMKIV such as sequestration of Ca2+/calmodulin.

The Presence of Mutant hCaMKIV in Thymocytes Results in a Developmental Defect

Figure 2B:
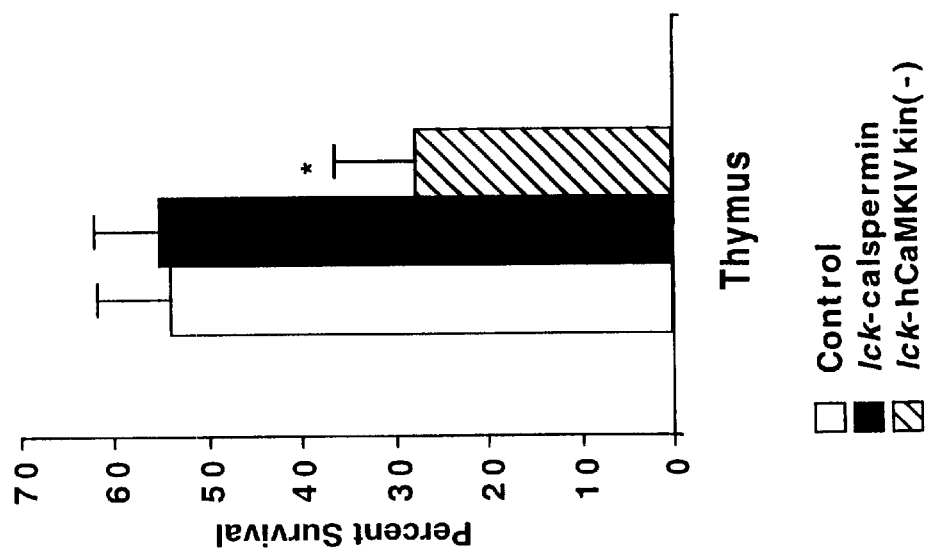
FIGS. 2A–2D.
Figure 2A:
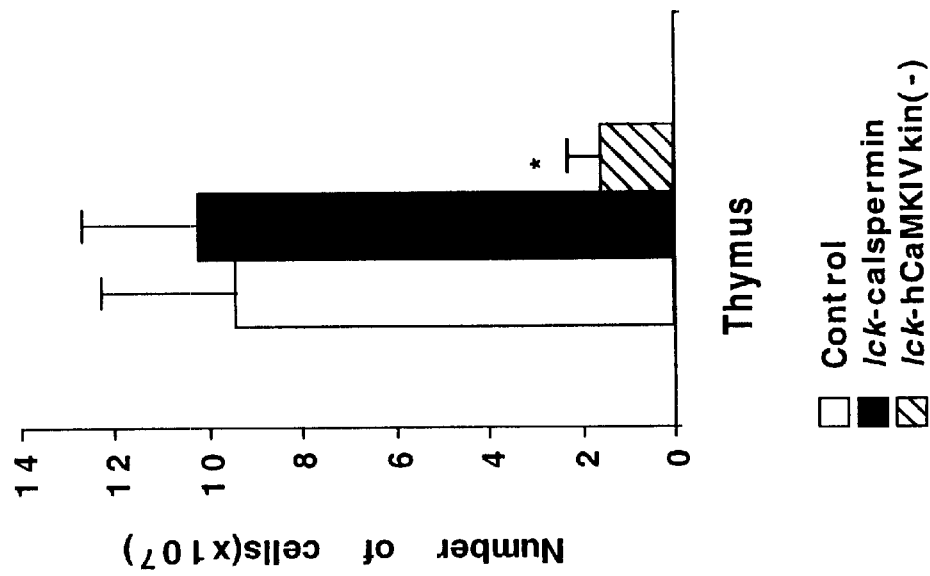
Figure 2D:
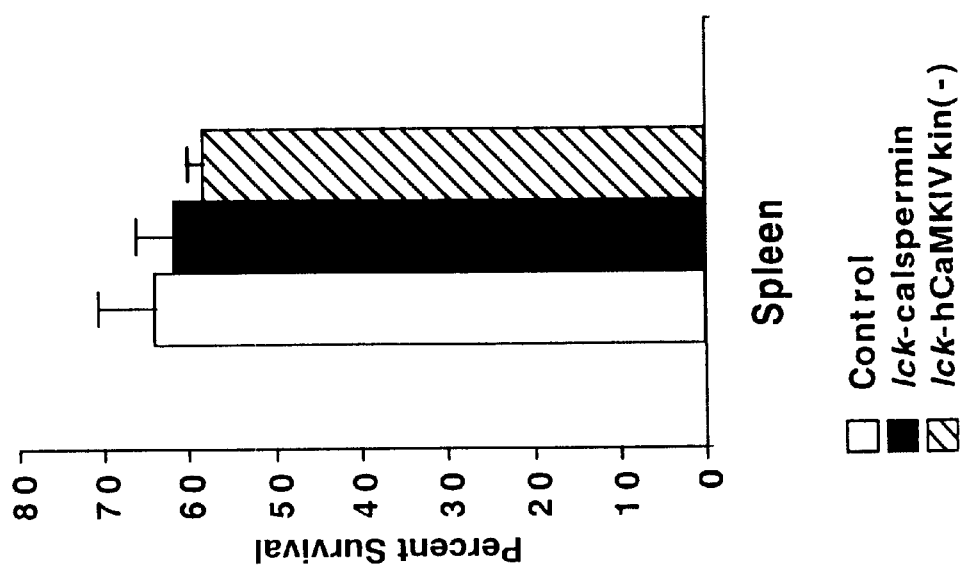
Figure 2C:
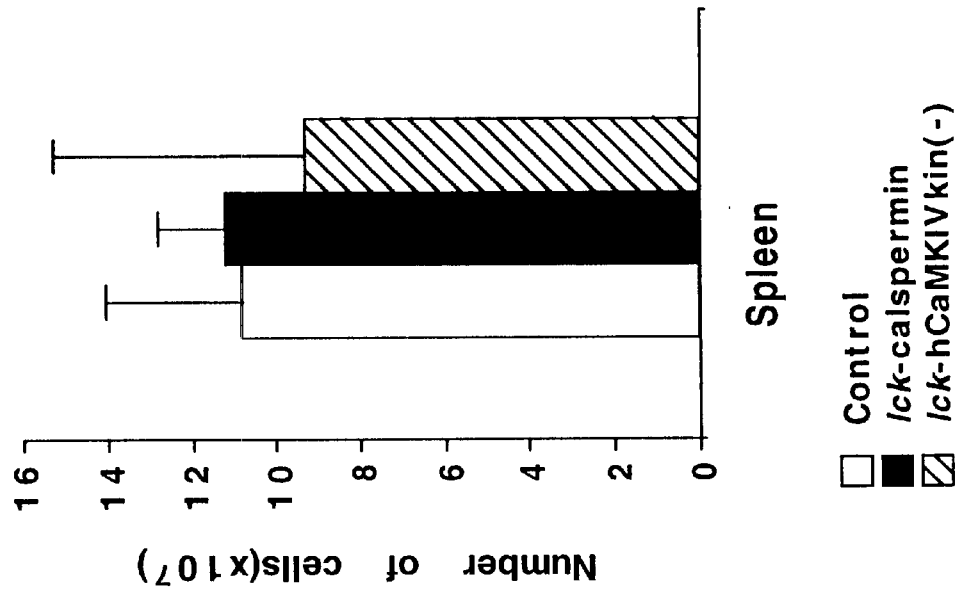
Figure 4A:
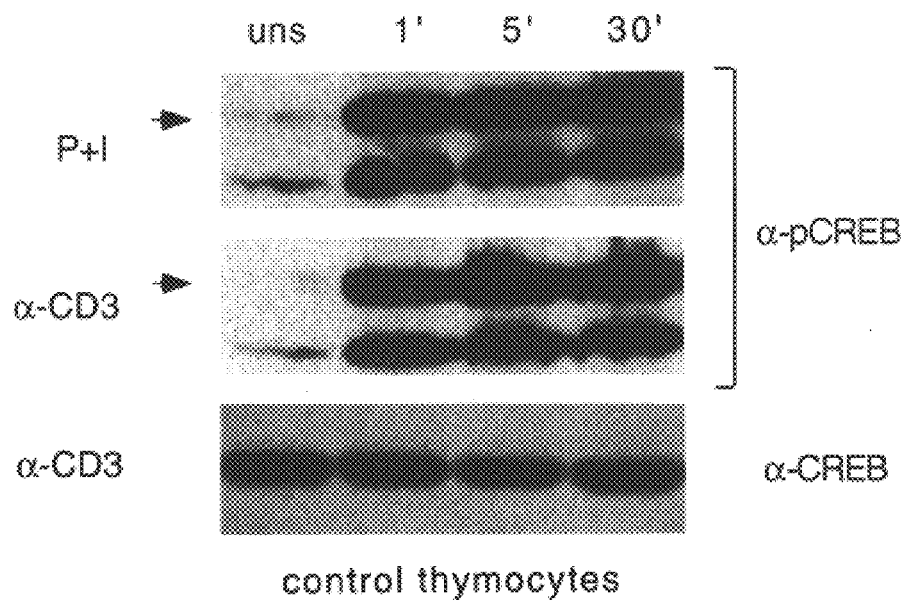
FIGS. 4A to 4F. CREB phosphorylation is inhibited in T cells that express mutant hCaMKIV.
Figure 4B:
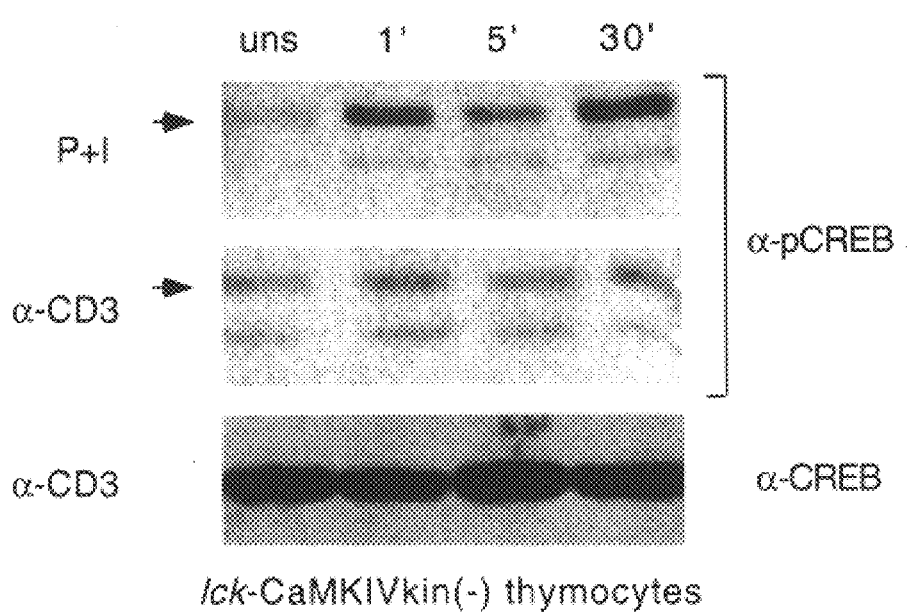
Figure 4C:
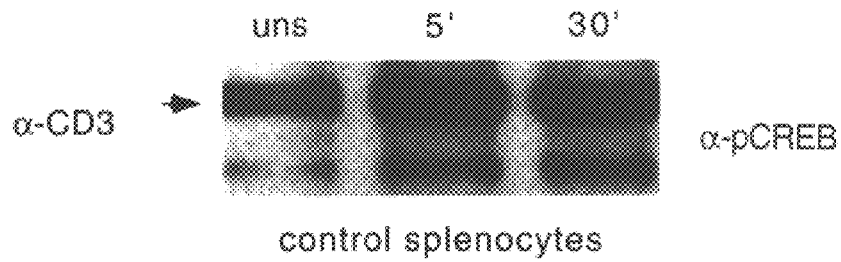
Figure 4D:
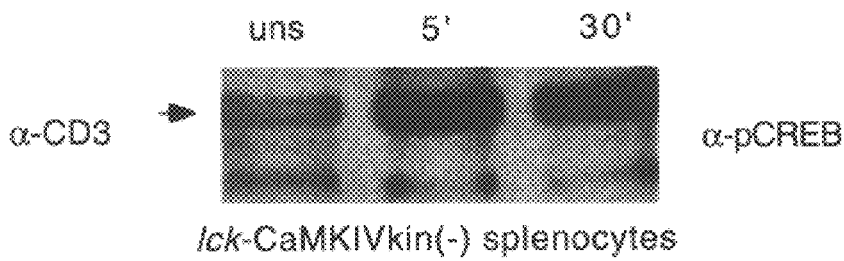
Figure 4E:
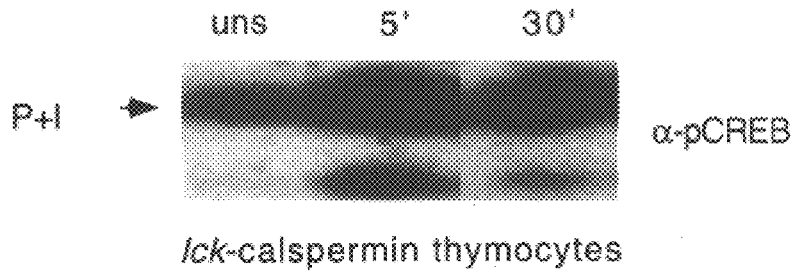
Figure 4F:
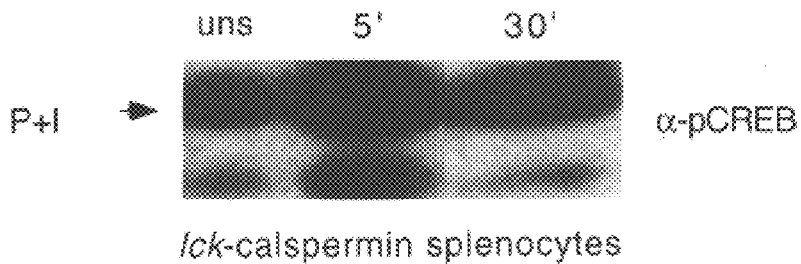

The most obvious phenotypic consequence resulting from the expression of the mutant hCaMKIV was a large reduction in the size and weight of the thymus. This gross phenotype was confirmed by analysis of the number of T cells resident in the thymus. As shown in FIG. 2A (left panel) the total number of thymocytes present in the thymus of transgenic mice is only about 16% of that found in the thymus of nontransgenic littermates or in transgenic mice that express calspermin (N=14, P<0.01). The deficit observed in the number of T cells in the thymus is completely normalized when the number of splenic cells is quantified. As shown in the left panel of FIG. 2B, no statistically significant difference exits between the number of splenocytes in control, transgenic hCaMKIV mutant (lck-CaMKIV Kin(−)) or transgenic calspermin (lck-calspermin) mice. This normalization in the spleen is entirely consistent with the fact that splenocytes cease expression of the hCaMKIV transgene.

One explanation for the decreased cellularity of the thymus could be that maturation of T cells within that organ is defective. To examine this question, flow cytometry was used to quantify the number and distribution of cells, based on the cell surface markers CD4 and CD8. The results of these experiments are shown as FIG. 3. Cells were isolated from the thymus or spleen and an equivalent number of live cells (4×106) was aliquoted based on trypan blue exclusion followed by counting in a hemocytometer. Thymic cells are shown in the top row of panels in FIG. 3. Thymocytes that do not contain either cell surface marker are called double-negative and are distributed in the lower left quadrant. Double positive cells (CD4/CD8) are found in the upper right quadrant. CD4 positive cells are sorted in the upper left and CD8 positive in the lower right. The numbers in the quadrants represent the percent of the total cells that are scored in that quadrant. It is readily seen that there are no differences in the distribution of T cells in the thymus of hCaMKIV mutant, calspermin or control mice. The lower row of panels shows the same experiment carried out on splenocytes from the identical mice. Only single positive CD4 or CD8 T cells exit the thymus to become stored in the spleen. So, the quadrants to compare are the upper left (CD4) and lower right (CD8). Again no differences are apparent between any of the three animals. The largest number of cells present in the spleen are B lymphocytes and are scored in the lower left quadrant as they do not express either the CD4 or CD8 surface antigens.

The data in FIG. 3 suggest that development and maturation of T cells are not impaired in the mice expressing the mutant hCaMKIV. However, the ability to generate or maintain normal numbers of T cells during development has been compromised. This decreased cellularity could result from either a significant defect in proliferation and/or an increased rate of cell death of thymic T cells. The first attempt to address this question was to employ a cell survival assay. These results for thymic and splenic T cells are presented in the upper and lower right hand histograms of FIG. 2, respectively. Primary culture conditions wre used such that 50–60% of T cells from the control mice will survive a 30 hr. incubation. Whereas there is no difference between normal thymic T cells and those expressing calspermin, cells containing the mutant hCaMKIV undergo a much greater rate of spontaneous apoptosis (N=34, P<0.01). This defect is not apparent in cells isolated from the spleen, a result entirely consistent with the observation that splenic T cells no longer express the transgene product. Thus at least one explanation for the decreased cellularity found in the thymus of the mice expressing the mutant form of CaMKIV could be that they die more rapidly, at least in cell culture.

The Presence of Mutant hCaMKIV Results in a T Cell Signaling Defect

It has been shown that CaMKIV is activated within seconds following engagement of the T cell receptor (17, 23, 32). Similarly, CREB is rapidly phosphorylated in response to a T cell activating signal (15). Since CaMKIV phosphorylates CREB on Ser-133 (19, 20, 21), it was determined whether the T cells that expressed the mutant hCaMKIV might have an altered ability to phosphorylate CREB. The results of a representative experiment are shown in FIG. 4. As can be seen in the top left hand panel, addition of phorbol ester (PMA) and ionomycin (shown as P/I as in the figure) to thymic T cells from normal mice resulted in robust phosphorylation of CREB by one min. This signal was maintained for at least 30 min. The Ser-133 phosphorylated form of CREB was selectively examined by the use of an antibody that only recognizes this phosphorylated epitope (33). Similar results were obtained when the cells were stimulated by addition of the anti-CD3 antibody which produces the signal through engagement of the T cell receptor (a-CD3). The location of the phosphoCREB signal is depicted by an arrow. Note that a faster migrating protein also shows an increased phosphorylation in response to addition of P/I or a-CD3. This protein has been provisionally identified as ATF1, another member of the CREB family of transcription factors because: a) the phosphorylated form of ATF1 is known to be recognized by the phosphoCREB antibody; b) it is the same size as ATF1 based on migration in an SDS gel; and c) ATF1 has also been shown to be present in T cells (15) and can be phosphorylated and activated by CaMKIV (34). The third autoradiogram on the right shows that there was no change in the total amount of CREB during the 30 min. of the experiment by use of an antibody that recognizes both phosphorylated and unphosphorylated CREB (α-CREB).

The right panels at the top of FIG. 4 show the results obtained when T cells containing the mutant hCaMKIV were stimulated with P/I or a-CD3. Very little phosphorylation of CREB was observed at any of the 3 time points in response to either stimulus. In the case of ATF1, it was not possible to demonstrate any increase in phosphorylation. The third autoradiogram shows that equivalent amounts of CREB were present at all time points. Comparison of the α-CREB blots between the normal and mutant hCaMKIV-containing cells shows that the protein is also present in similar amounts in T cells from both types of mice. The abrogation of CREB phosphorylation characteristic of thymocytes from mice expressing the mutant hCaMKIV was not observed in T cells containing the calspermin protein. Shown in the middle panels of FIG. 4 is CREB phosphorylation in splenic T cells in response to α-CD3. Cells from both control and mutant hCaMKIV mice show similar increases in phosphorylation of CREB. The recovery of a normal response in cells from the transgenic mice is again consistent with the fact that splenocytes no longer contain the mutant hCaMKIV protein. Finally, the bottom panels of FIG. 4 show that the presence of calspermin does not affect phosphorylation of CREB in response to P/I stimulation. It was concluded that the presence of the mutant enzyme must result in a dominant/negative effect on CREB phosphorylation whether the stimulus is physiologically relevant like α-CD3 or more general as elicited by the combination of PMA and ionomycin.

Figure 5A:
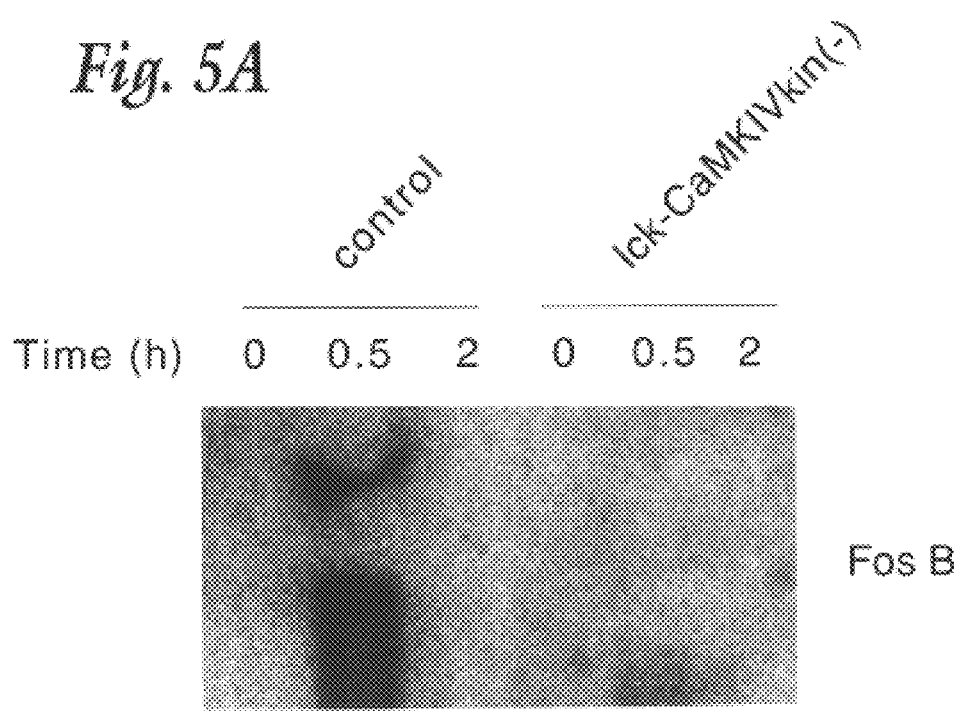
FIGS. 5A and 5B. Fos B induction is inhibited in T cells that express mutant hCaMKIV. Thymocytes from control and lck-CaMKIVkin(−) transgenic mice were stimulated with PMA+ionomycin for the indicated time. Total RNA was then extracted and subjected to northern blot analysis using a Fos B-specific probe. To assess RNA sample loading the blot was striped and reanalyzed with a probe for glucose-3-phosphate dehydrogenase (GAPDH). Shown is one representative experiment. (n=2).
Figure 5B:
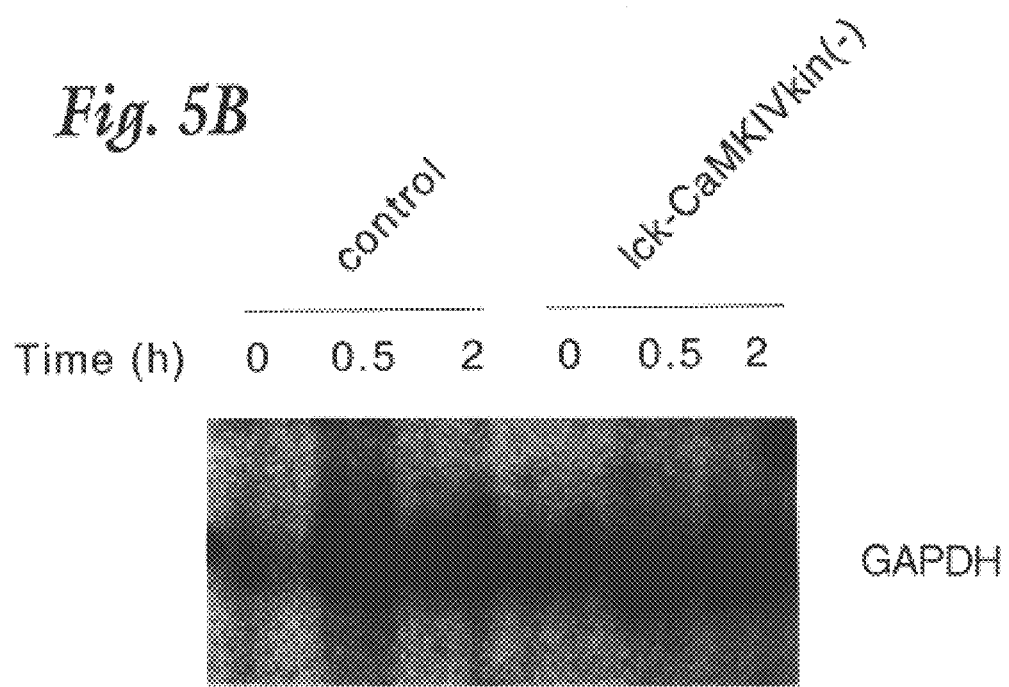

CREB phosphorylation in thymic T cells is required for the activation of the immediate early genes cfos, Fra-2 and Fos B (15). Therefore, the appearance of Fos B mRNA in response to T cell stimulation was examined. As shown in FIG. 5, stimulation of control T cells with α-CD3 resulted in transient expression of Fos B mRNA. The time course of this response and the presence of the two mRNA species are identical to the results reported by Barton et al., (15). However, cells that express the mutant hCaMKIV fail to demonstrate an increase in Fos B mRNA in response to stimulation. The northern blot was stripped and reprobed with a GAPDH cDNA. The bottom autoradiogram in FIG. 5 shows that each lane did contain equivalent amounts of RNA. Thus the presence of the mutant hCaMKIV correlates with the inability to phosphorylate CREB and to produce Fos B mRNA.

Figure 6A:
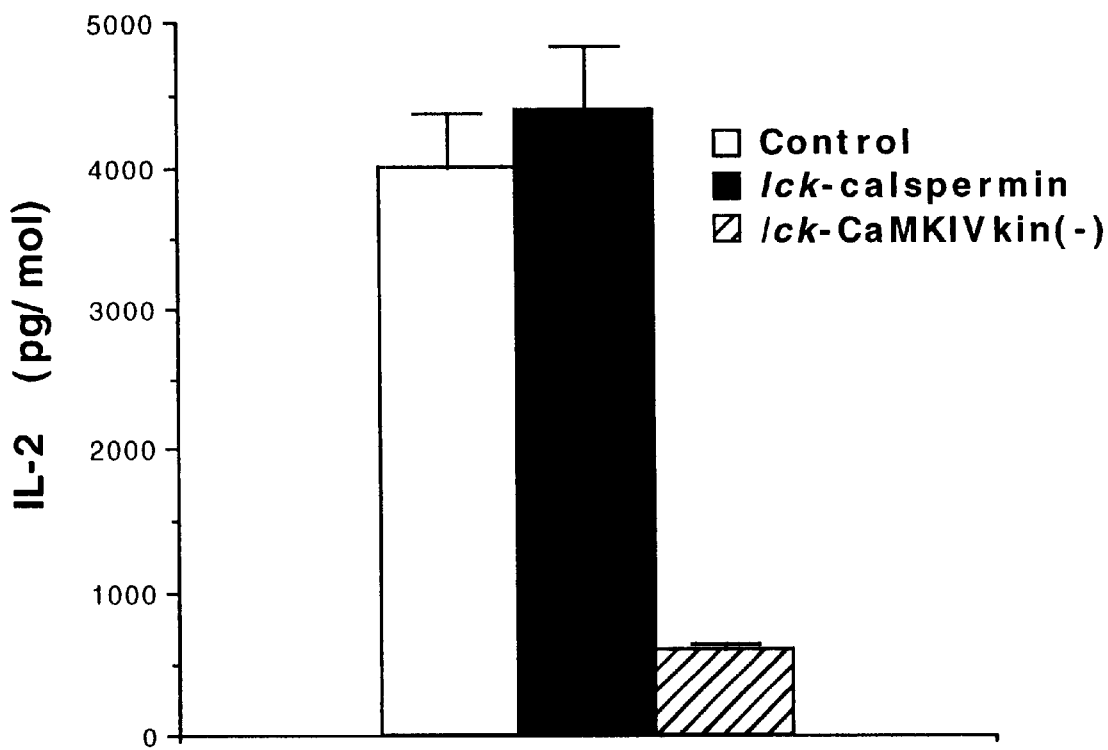
FIGS. 6A to 6D. Induction of IL-2 and IL-2Ra are inhibited in T cells that express mutant hCaMKIV.
Figure 6B:
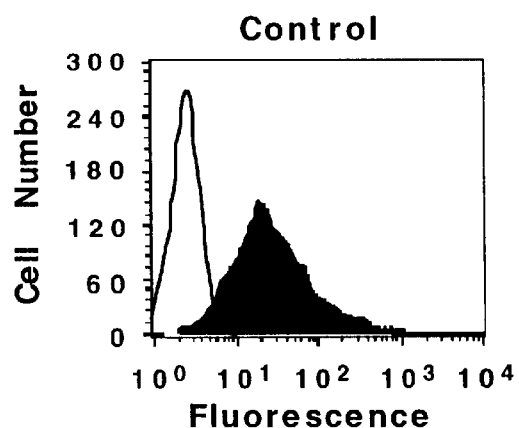
Figure 6C:
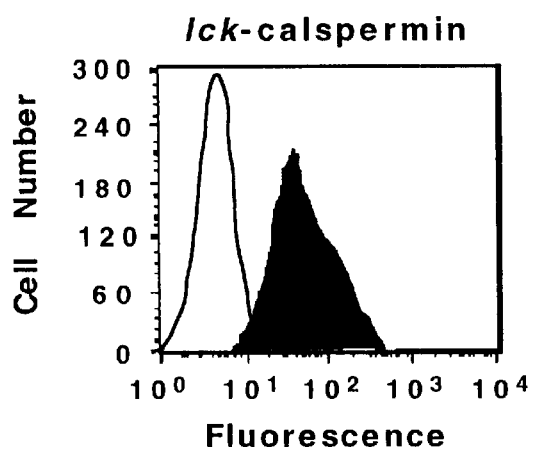
Figure 6D:
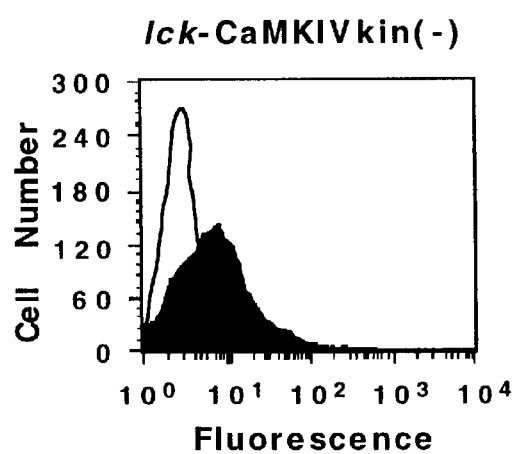

The CREB/AP 1 pathway has been shown to be critical for the production of IL-2 (15). FIG. 6A shows that whereas a 48 hr. stimulation of T cells from control or calspermin transgenic mice produce equivalent amounts of IL-2 in response to α-CD3, very little of the cytokine is made by the cells that contain the mutant hCaMKIV. As one consequence resulting from T cell activation is an increase in the number of cells that express the IL-2 receptor (15, 35, 36), we also examined the appearance of the a chain of the IL-2 receptor (CD25) 30 hr after cells were challenged with a mitogenic stimulus. The results, shown in FIG. 6B, show a similar response of control and calspermin-containing cells but a considerable reduction in cells that express mutant hCaMKIV. Qualitative analysis of the data suggest that the former two cell populations show about a 10-fold increase in the proportion that contain CD25, whereas less than a 3-fold increase is seen in the cells containing mutant hCaMKIV.

The data presented in FIGS. 4–6 are representative experiments. Each experiment was repeated several times with T cells from different transgenic mice. Because of the small numbers of such cells, it was not possible to conduct each experiment on cells from the same animals. Therefore, considerable variation was observed from animal to animal. This is due to the fact that the T cells contained differing amounts of the mutant hCaMKIV. A consistent observation was that the magnitude of the inhibitory responses was directly proportional to the amount of CaMKIV. In addition, when it was possible to carry out two assays on cells from the same animal, the proportional differences were identical when comparing CREB phosphorylation to IL-2 production or to the decrease in the number of cells expressing CD25. For example if CREB phosphorylation was decreased by 95%, similar percent decreases were found in either of the other two parameters. Based on these observations, it is believed that the 4 events, CREB phosphorylation, induction of Fos B mRNA, IL-2 production and the expression of CD25 are related to each other and are coincidentally down-regulated by the presence of the mutant hCaMKIV.

Example II
Expression of CaMKIV kin(-) in T Cells of Transgenic Mice

To examine the role of CaMKIV in T cells, transgenic mice were generated in which expression of a kinase minus version of CaMKIV was targeted to thymocytes. Since CaMKIV is not detectable at day 15 of embryonic development (E15), a T cell specific promoter was used that is expressed prior to this developmental time. The choice was the proximal promoter for the proto-oncogene lck. This promoter has been shown to target T cell specific expression in transgenic mice (Chaffin et al, EMBO J. 9:3821 (1990)) and, whereas it is not known precisely when the promoter becomes active during development of the thymus, it is expressed by E15 (Reynolds et al, Mol. Cell. Biol. 10:4266 (1990)). Thus, the utilization of the lck promoter maximizes any consequences of expressing the kinase minus CaMKIV since the transgene would be expressed prior to the endogenous gene during thymic development. In addition, the proximal lck promoter is active at all stages of T cell development in the thymus but is silenced when cells are released into the circulation and is also inactive in thymocytes that are present in the spleen (Chaffin et al, EMBO J. 9:3821 (1990)).

A lck promoter construct first characterized by Chaffin et al (EMBO J. 9:3821 (1990)) was used to target expression of CaMKIV or a kinase minus mutant form of CaMKIV to thymocytes in transgenic mice. A line of mice has been developed that expresses about 2.5 fold more kin(-) protein than endogenous CaMKIV.

Remarkable effects were observed in the analysis of 25 day old animals. First, the thymus size was decreased by 75% relative to mice that overexpressed the w+ CaMKIV. This decrease in size was due to a similar % reduction in the total number of cells resident in the thymus. Second, the remaining T cell population contained a much greater proportion than normal of dead cells. Cell sorting analysis confirmed that an increased number of apoptotic cells was present. However, in the live cell population, no gross differences in CD+, CD8+ or double positive cells were apparent. The number and cell surface marker distribution of splenic T cells were normal, suggesting no defect in the export of cells from the thymus. These findings indicate that if the kin(-) protein is acting in a dominant/negative way, then the presence of active CaMKIV could either select against apoptosis or be required for proliferation. It is unclear how kin(-) could behave as a dominant/negative but a similar effect of a kinase minus form of the MAP kinase, MEK-1, has been observed in mice using the same lck promoter based construct (Alberola-Ila et al, Nature 373:320 (1995)). In the case of the MEK-1 kin(-), positive selection of T cells was inhibited as the very specific phenotype. In the present case, the results indicate that either saturation of a CaMKIV binding protein is occurring or inhibition of nuclear entry (and/or interactions) of the kinase is being effected. The fact that the lck promoter is expressed earlier in development than is CaMKIV creates ideal conditions to generate a dominant/negative effect.

The presence of the mice expressing the kin(-) CaMKIV in the thymocytes provided the opportunity to determine if the remaining live cells behaved differently in culture. Live cells were quantified and placed in culture. When thymic T cells were cultured in serum-containing medium they did not proliferate as they lack the co-stimulatory signals discussed above. Rather they undergo spontaneous apoptosis in a time-dependent manner. Incubation of T cells from a normal mouse for 30 hr. results in about 40% of the cells undergoing apoptosis. However, only 15% of the cells from the mice expressing the CaMKIV kin(-) protein survive. Thus the presence of kin(-) correlates with a 3-fold increase in the rate of spontaneous apoptosis. To examine whether CaMKIV plays a role in T cell activation, cells expressing kin(-) were stimulated with anti-CD3 antibody, phorbol ester, ionomycin or combinations of phorbol ester and ionomycin and IL-2 production evaluated. The cells secreted 6-fold less IL-2 in response to these treatments compared to T cells from normal mice of the same age. Similarly, phosphorylation of CREB was markedly attenuated when cells were challenged with agents that increased intracellular $Ca^{2+}$ or activate PKC. These experiments indicate that CaMKIV is a CREB kinase in T cells and that this phosphorylation event provides a signal necessary for an early event in the cascade of reactions that result in T cell activation.

Figure 7:
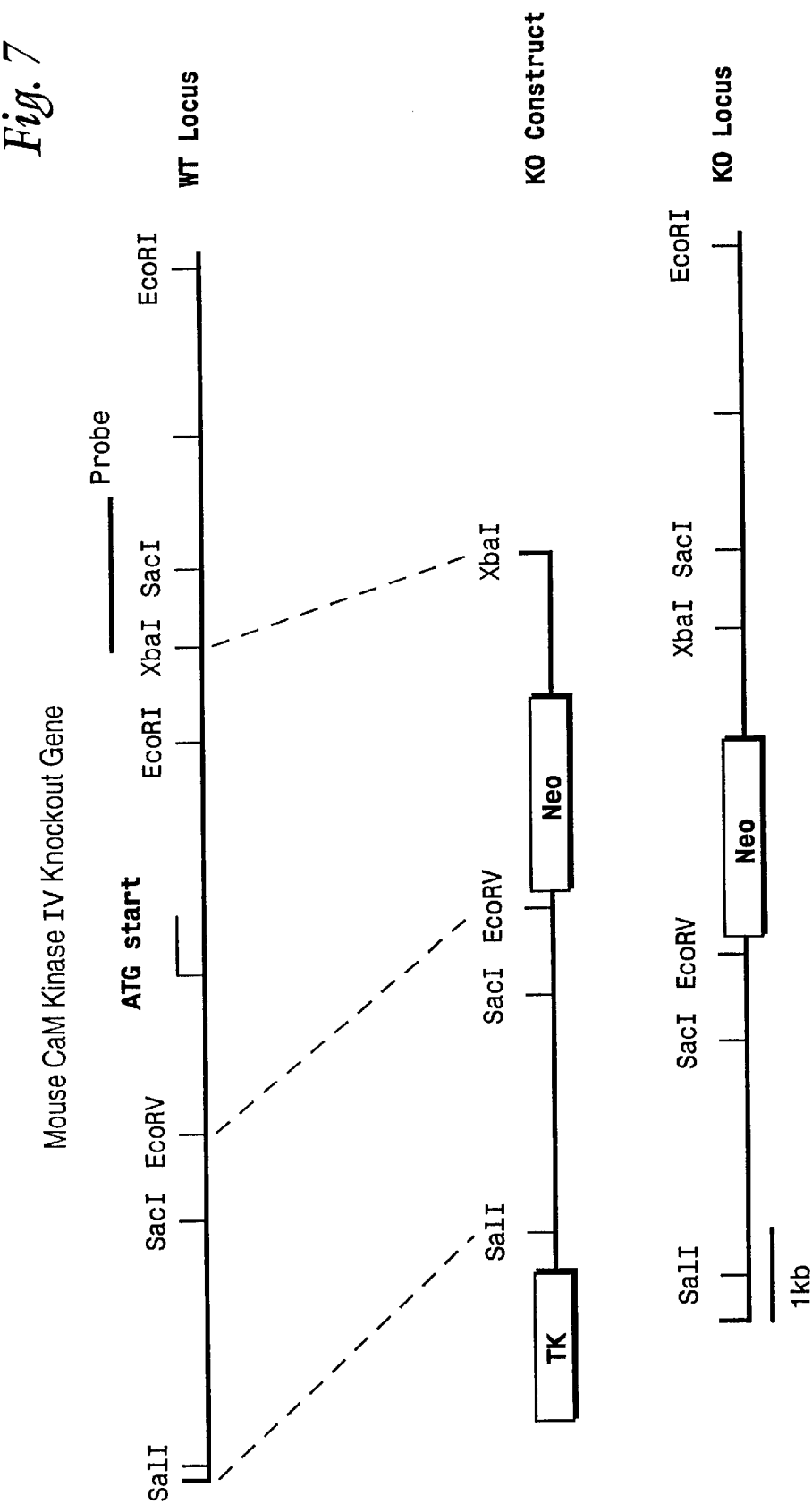
FIG. 7 Construct prepared for use in mouse CaMKIV knockout gene studies.

Example III
Disruption of the CaMKIV Gene in Mice by Homologous Recombination Mice in which the CaMKIV gene is silenced by homologous recombination have been produced. The DNA construct used to delete a portion of the gene in embryonic stem cells is shown in FIG. 7. The construct was prepared in collaboration with G. Stanley McKnight (University of Washington, Seattle). The construct was electroporated into embryonic stem cells at the NC Transgenic facility at UNC under the direction of Dr. Beverly Koller. The microinjection of the cells into blastocysts and the creation of the original founder mice was also done in that facility.

The primary phenotype of the first group of mice that are nullizygous for the CaMKIV locus, that is relevant to the invention, is that the mice lose all their hair within the first two weeks of life and appear very similar to nude mice. In the nude mouse, hair loss is directly related to the absence of T cells. These experiments confirm that CaMKIV is absolutely required for proper immune function and indicated that this enzyme is an excellent target for cell specific immunosuppressant drugs.

All documents cited above and below are hereby incorporated in their entirety by reference.

One skilled in the art will appreciate from a reading of this disclosure that various changes in form and detail can be made without departing from the true scope of the invention.

REFERENCES

1. Crabtree G R, Clipstone N 1994 Signal transmission between the plasma membrane and the nucleus of T lymphocytes. Annu Rev Biochem 63:1045–1076
2. Northrop J P, Ho S N, Chen L, Thomas K F, Nolan G P, Admon A, Crabtree G R 1994 NF-AT components define a family of transcription factors targeted in T-cell activation. Nature 369:497–502
3. Jain J, McCaffrey P G, Valge-Archer V E, Rao A 1992 Nuclear factor of activated T cells contains Fos and Jun. Nature 356:801–804
4. Castigli E, Chatila T A, Geha R S 1993 A protein of the AP-1 family is a component of the nuclear factor of activated T lymphocytes. J Immunol 150:3284–3290
5. Clipstone N A, Crabtree G R 1992 Identification of calcineurin as a key signaling enzyme in T lymphocyte activation. Nature 357:695–697
6. Ruff V A, Leach K L 1995 Direct demonstration of NFATp dephosphorylation and nuclear localization in activated HT-2 cells using a specific NFATp polyclonal antibody. J Biol Chem 270:22602–22607
7. Luo C, Shaw K T, Raghavan A, Aramburu J, Garcia-Cozar F, Perrino B A, Hogan P G, Rao A 1996 Interaction of calcineurin with a domain of the transcription factor NFAT1 that controls nuclear import. Proc Natl Acad Sci USA 93:8907–8912
8. Shaw K T, Ho A M, Raghavan A, Kim J, Jain J, Park J, Sharma S, Rao A, Hogan P G 1995 Immunosuppressive drugs prevent a rapid dephosphorylation of transcription factor NFAT1 in stimulated immune cells. Proc Natl Acad Sci USA 92:11205–11209
9. Schwartz R H 1990 A cell culture model for T lymphocyte clonal anergy. Sceince 248:1349–1356
10. Nghiem P, Ollick T, Gardner P, Schulman H 1994 Interleukin-2 transcriptional block by the multifunctional Ca2+/calmodulin kinase. Nature 371:347–350
11. Hama N, Paliogianni F, Fessler B J, Boumpas D T 1995 Calcium/calmodulin-dependent protein kinase II down-regulates both calcineurin and protein kinase C-mediated pathways for cytokine gene expression. J Exp Med 181:1217–22
12. Ullman K S, Northrop J P, Admon A, Crabtree G R 1993 Jun family members are controlled by a calcium-regulated, cyclosporin A-sensitive signaling pathway in activated T lymphocytes. Genes Dev 7:188–196
13. Sheng M, Greenberg M E 1990 The regulation and function of c-fos and other immediate early genes in the nervous system. Neuron 4:477–485
14. Gonzalez G A, Montminy M R 1989 Cyclic AMP stimulates somatostatin gene transcription by phosphorylation of CREB at serine 133. Cell 59:675–680
15. Barton K, Muthusamy N, Chanyangam M, Fischer C, Clendenin C, Leiden J M 1996 Defective thymocyte proliferation and IL-2 production in transgenic mice expressing a dominant-negative form of CREB. Nature 379:81–85
16. Frangakis M V, Chatila T, Wood E R, Sahyoun N 1991 Expression of a neuronal Ca2+/calmodulin-dependent protein kinase, CaM kinase-Gr, in rat thymus. J Biol Chem 266:17592–17596
17. Hanissian S H, Frangakis M, Bland M M, Jawahar S, Chatila T A 1993 Expression of a Ca2+/calmodulin dependent protein kinase, CaM kinase-Gr, in human T lymphocytes. Regulation of kinase activity by T cell receptor signaling. J Biol Chem 268:20055–20063
18. Jensen K F, Ohmstede Calif., Fisher R S, Sahyoun N 1991 Nuclear and axonal localization of Ca2+/calmodulin-dependent protein kinase type Gr in rat cerebellar cortex. Proc Natl Acad Sci USA 88:3850–2853
19. Sun P, Enslen H, Myung P S, Maurer R A 1994 Differential activation of CREB by Ca2+/calmodulin-dependent protein kinases type II and type IV involves phosphorylation of a site that negatively regulates activity. Genes Dev 8:2527–2539
20. Enslen H, Sun P, Brickey D, Soderling S H, Klamo E, Soderling T R 1994 Characterization of Ca2+/calmodulin-dependent protein kinase IV; role in transcription regulation. J Biol Chem 269:15520–15527
21. Matthews R P, Guthrie C R, Wailes L M, Zhao X, Means A R, McKnight G S 1994 Calcium/calmodulin-dependent protein kinase types II and IV differentially regulate CREB-dependent gene expression. Mol Cell Biol 14:6107–6116
22. Ho N, Gullberg M, Chatila T 1996 Activation protein 1-dependent transcriptional activation of interleukin 2 gene by Ca2+/calmodulin kinase type IV/Gr. J Exp Med 184:101–112
23. Chatila T, Anderson K A, Ho N, Means A R 1996 A Unique phosphorylation-dependent mechanism for the activation of Ca2+/calmodulin-dependent protein kinase type IV/Gr. J Biol Chem 271:21542–21548
24. Bito H, Deisseroth K, Tsien R W 1996 CREB Phosphorylation and dephosphorylation: a Ca2+-and stimulus duration-dependent switch for hippocampal gene expression. Cell 87:1203–1214.
25. Allen J M, Forbush K A, Perlmutter R M 1992 Functional dissection of the lck proximal promoter. Mol Cell Biol 12:2758–2768
26. Reynolds P J, Lesley J, Trotter J, Schulte R, Hyman R, Sefton B M 1990 Changes in the relative abundance of type I and type II lck mRNA transcripts suggest differential promoter usage during T-cell development. Mol Cell Biol 10:4266–4270
27. Chaffin K E, Beals C R, Wilkie T M, Forbush K A, Simon M I, Perlmutter R M 1990 Dissection of thymocyte signaling pathways by in vivo expression of pertussis toxin ADP-ribosyltransferase. EMBO 9:3821–3829
28. Selbert M A, Anderson K A, Huang Q H, Goldstein E G, Means A R, Edelman A M 1995 Phosphorylation and activation of Ca2+-calmodulin-dependent protein kinase IV by Ca2+-calmodulin-dependent protein kinase Ia kinase; phosphorylation of threonine 196 is essential for activation. J Biol Chem 270:17616–17621

29. Ono T, Slaughter G R, Cook R G, Means A R 1989 Molecular cloning, sequence and distribution of rat calspermin, a high affinity calmodulin-binding protein. J Biol Chem 264:2081–2087
30. Means A R, Cruzalegui F, LeMagueresse B, Needleman D S, Slaughter G R, Ono T 1991 A novel Ca2+/calmodulin-dependent protein kinase and a male germ cell-specific calmodulin-binding protein are derived from the same gene. Mol Cell Biol 11:3960–3971
31. Sun Z, Sassone-Corsi P, Means A R 1995 Calspermin gene transcription is regulated by two cyclic AMP response elements contained in an alternative promoter in the calmodulin kinase IV gene. Mol Cell Biol 15:561–571
32. Park I K, Soderling T R 1995 Activation of Ca2+/calmodulin-dependent protein kinase (CaM-kinase) IV by CaM-kinase kinase in Jurkat T lymphocytes. J Biol Chem 270:30464–30469
33. Ginty D D, Kornhauser J M, Thompson M A, Bading H, Mayo K E, Takahashi J S, Greenberg M E 1993 Regulation of CREB phosphorylation in the suprachiasmatic nucleus by light and a circadian clock. Science 260:238–241
34. Sun P, Lou L, Maurer R A 1996 Regulation of activating transcription factor-1 and the cAMP response element-binding protein by Ca2+/calmodulin-dependent protein kinases type I, II, and IV. J Biol Chem 271:3066–3073
35. Carding S R, Hayday A C, Bottomly K 1991 Cytokines in T-cell development. Immunol Today 12:239–245
36. Fischer M, MacNeil I, Suda T, Cupp J E, Shortman K, Zlotnik A 1991 Cytokine production by mature and immature thymocytes. J Immunol 146:3452–3456.
37. Alberola-lla J, Forbush K A, Seger R, Krebs E G, Perlmutter R M 1995 Selective requirement for MAP kinase activation in thymocyte differentiation. Nature 373:620–623
38. Okuno S, Kitani T, Fujisawa H 1994 Purification and Characterization of Ca2+/calmodulin-dependent protein kinase IV kinase from rat brain. J Biochem 116:923–930
39. Enslen H, Tokumitsu H, Soderling T R 1995 Phosphorylation of CREB by CaM-kinase IV activated by CaM-kinase IV kinase. BBRC 207:1038–1043
40. Tokumitsu H, Brickey D A, Glod J, Hidaka H, Sikela J, Soderling T R 1994 Activation Mechanisms for Ca2+/calmodulin-dependent protein kinase IV. J Biol Chem 269:28640–28647
41. Tokumitsu H, Enslen H, Soderling T R 1995 Characterization of a Ca2+/calmodulin-dependent protein kinase cascade; molecular cloning and expression of calcium/calmodulin-dependent protein kinase kinase. J Biol Chem 270:19320–19324
42. Tokumitsu H, Soderling T R 1996 Requirements for calcium and calmodulin in the calmodulin kinase activation cascade. J Biol Chem 271:5617–5622
43. Edelman A M, Mitchelhill K I, Selbert M A, Anderson K A, Hook S S, Stapleton D, Goldstein E G, Means A R, Kemp B E 1996 Multiple Ca2+-calmodulin-dependent protein kinase kinases from rat brain; purification, regulation by Ca2+-calmodulin, and partial amino acid sequence. J Biol Chem 271:10806–10810
44. Enslen H, Tokumitsu H, Stork P J S, Davis R J, Soderling T R 1996 Regulation of mitogen-activated protein kinases by a calcium/calmodulin-dependent protein kinase cascade. Proc. Natl. Acad. Sci. USA 93:10803–10808.
45. Krebs J, Means R L, Honegger P 1996 Induction of calmodulin kinase IV by the thyroid hormone during the development of rat brain. J Biol Chem 271:11055–11058
46. Montgomery R A, Dallman M J 1991 Analysis of cytokine gene expression during fetal thymic ontogeny using the polymerase chain reaction. J Immunol 147:554–560
47. Zuniga-Pflucker J C, Schwartz H L, Lenardo M J 1993 Gene transcription in differentiating immature T cell receptorneg thymocytes resembles antigen-activated mature T cell. J Exp Med 178:1139–1149
48. Chen J, Stewart V, Spyrou G, Hilberg F, Wagner E F, Alt F W 1994 Generation of normal T and B lymphocytes by c-jun deficient embryonic stem cells. Immunity 1:65–72
49. Crompton T, Gilmour K C, Owen M J 1996 The MAP kinase pathway controls differentiation from double-negative to double-positive thymocyte. Cell 86:243-251
50. Hogan B. Beddington R, Costantini F, Lacy E 1994 Manipulating the mouse embryo-A Laboratory Manual-:second edition. Cold Spring Harbor Laboratory Press. Cold Spring Harbor, N.Y.
51. Ribar T J, Epstein P N, Overbeek P A, Means A R 1995 Targeted overexpression of an inactive calmodulin that binds Ca2+ to the mouse pancreatic B-cell results in impaired secretion and chronic hyperglycemia. Endocrinology 136:106–115
52. Garvin A M, Abraham K M, Forbush K A, Farr A G, Davison B L, Perlmutter R M 1990 Disruption of thymocyte development and lymphogenesis induced by SV40 T-antigen. Int Immunol 2:173–180
53. Laemmli U K 1970 Cleavage of structural proteins during the assembly of the head of bacteriophage t4. Nature 227:680–685

What is claimed is:

1. A method of screening a test compound for potential as an immunosuppressive drug candidate comprising:

i) contacting $Ca^{2-}$/calmodulin-dependent protein kinase IV (CaMKIV) and a substrate therefor in the presence of said test compound, CaMKIV kinase, calmodulin and calcium, under conditions such that CaMKIV-dependent phosphorylation of said substrate can be effected, and ii) determining the level of phosphorylation of said substrate resulting from step (i) and comparing said level with a level of phosphorylation of said substrate obtained in the absence of said test compound, wherein a reduction in the level of phosphorylation of said substrate in the presence of said test compound indicates that said compound has potential as an immunosuppressive drug candidate.

2. The method according to claim 1 wherein said substrate is a peptide substrate.

3. The method according to claim 1 wherein said CaMKIV and said substrate are present in a cell free system.

4. The method according to claim 1 wherein said CaMKIV and said substrate are present in an isolated cell.

5. The method according to claim 1 wherein, in step (i), said conditions are such that CaMKIV kinase dependent phosphorylation of CaMKIV can be effected.

6. The method according to claim 5 wherein, in step (ii), the level of phosophorylation of CaMKIV is determined and compared with a level of phosphorylation of CaMKIV obtained in the absence of said test compound, wherein a reduction in the level of phosphorylation of said CaMKIV in the presence of said test compound indicates that said compound has potential as an immunosuppressive drug candidate.

7. The method according to claim 4 wherein said cell is a T cell.

* * * * *